United States Patent
Hsieh (10) Patent No.: US 6,587,537 B1
(45) Date of Patent: Jul. 1, 2003

(54) METHODS AND APPARATUS FOR MULTI-SLICE IMAGE RECONSTRUCTION

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/113,069

(22) Filed: Apr. 1, 2002

(51) Int. Cl.$^7$ .................................................. A61B 6/03
(52) U.S. Cl. ............................ 378/4; 378/15; 378/901
(58) Field of Search ..................... 378/4, 8, 15, 19, 378/901

(56) References Cited

U.S. PATENT DOCUMENTS

| | | |
|---|---|---|
| 5,115,394 A | 5/1992 | Walters |
| 5,276,614 A | 1/1994 | Heuscher |
| 5,301,037 A | 4/1994 | Kang et al. |
| 5,384,861 A | 1/1995 | Mattson et al. |
| 5,416,815 A | 5/1995 | Hsieh |
| 5,473,656 A | 12/1995 | Hsieh |
| 5,491,735 A | 2/1996 | Hsieh |
| 5,515,409 A | 5/1996 | Hsieh |
| 5,533,091 A | 7/1996 | Hsieh |
| 5,610,963 A | 3/1997 | Hsieh |
| 5,708,690 A | 1/1998 | Hsieh |
| 5,732,118 A | 3/1998 | Hsieh |
| 5,774,601 A * | 6/1998 | Mahmoodi ................. 382/298 |
| 5,805,721 A | 9/1998 | Vuylsteke |
| 5,818,896 A | 10/1998 | Hsieh |
| 5,828,718 A | 10/1998 | Ruth et al. |
| 5,907,593 A | 5/1999 | Hsieh |
| 6,023,494 A | 2/2000 | Senzig |
| 6,101,234 A | 8/2000 | Ali |
| 6,137,856 A | 10/2000 | Lin |
| 6,173,032 B1 | 1/2001 | Besson |
| 6,233,308 B1 | 5/2001 | Hsieh |
| 6,269,139 B1 | 7/2001 | Hsieh |
| 6,272,200 B1 * | 8/2001 | Pan et al. ..................... 378/15 |
| 6,285,732 B1 | 9/2001 | Hsieh |
| 6,332,013 B1 | 12/2001 | Hsieh |

* cited by examiner

Primary Examiner—David V. Bruce
(74) Attorney, Agent, or Firm—Carl B. Horton, Esq.; Armstrong Teasdale LLP (57) ABSTRACT

A method for generating an adaptively interpolated projection of an object with an imaging system includes generating a first projection using a first interpolation kernel, generating a second projection using a second interpolation kernel, different from the first interpolation kernel, and taking a difference between the first projection and the second projection to generate a differential signal.

32 Claims, 4 Drawing Sheets

Examples of image artifacts produced by existing algorithms
Both scans were acquired with 8x1.25mm at pitch 13.4:1.

Images reconstructed with a high-order polynomial interpolation

Images reconstructed with the adaptive interpolation

ND APPARATUS FOR MULTI-
SLICE IMAGE RECONSTRUCTION

BACKGROUND OF THE INVENTION

This invention relates to computed tomographic (CT) imaging, and more particularly to methods and apparatus for reducing imaging artifacts in image generated using a multi-slice CT imaging system.

Some known helical algorithms use helical weighting functions that are determined based on the geometric information of a scanner. In other words, the weighting function does not change from scan-to-scan or patient-to-patient, as long as the scanning protocol remains the same. Although these algorithms have been performing somewhat satisfactorily in a clinical setting, recent investigations have revealed severe image artifacts. Studies have shown that all of the existing algorithms perform roughly the same in terms of image artifacts. Traditionally, these artifacts are suppressed by applying a low-pass filtering along the z-axis. The low-pass filtering can be carried out either in the projection space or in the image space. This approach, however, merely trades off image artifacts with the slice thickness. In order to achieve reasonable artifact suppression, a 20% or more degradation in slice thickness is encountered.

BRIEF DESCRIPTION OF THE INVENTION

In one aspect, a method for generating an adaptively interpolated projection of an object with an imaging system is provided. The method includes generating a first projection using a first interpolation kernel, generating a second projection using a second interpolation kernel, different from the first interpolation kernel, and taking a difference between the first projection and the second projection to generate a differential signal.

In another aspect, a computer to generate an adaptively interpolated projection of an object with a scanning imaging operable in at least one of a high speed data acquisition mode and a high quality data acquisition mode is provided. The computer is programmed to generate a first projection using a first interpolation kernel, generate a second projection using a second interpolation kernel, different from the first interpolation kernel, and take a difference between the first projection and the second projection to generate a differential signal.

In a further aspect, a computed tomographic (CT) imaging system for generating an adaptively interpolated projection of an object is provided. The CT system includes a detector array, at least one radiation source, and a computer coupled to the detector array and the radiation source. The computer is configured to generate a first projection using a first interpolation kernel, generate a second projection using a second interpolation kernel, different from the first interpolation kernel, take a difference between the first projection and the second projection to generate a differential signal, filter the differential signal using a low-pass filter, and map the filtered differential signal to a scaling function to generate an adaptively interpolated projection.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two dimensional slice taken through the object. Alternatively, a new projection is first interpolated from the original projection and a filtered backprojection algorithm is then used on the new projection to produce a reconstructed image.

Figure 1:
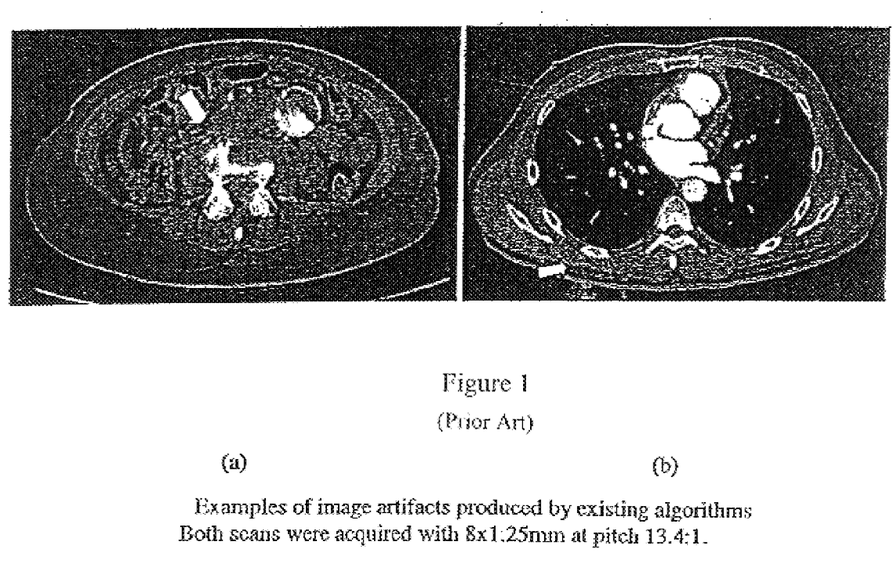
FIG. 1 is a prior art sinogram view of image artifacts produced by a known algorithm.

FIG. 1 is a sinogram view of a plurality of image artifacts produced by a known algorithm using an eight-slice scanner with 8×1.25 millimeter (mm) mode at a pitch of 13.4:1. In one known imaging system, using a known multi-slice helical reconstruction algorithm, a set of projections is estimated at the plane-of-reconstruction. The estimation can be performed either by physically obtaining a set of interpolated projection data, or by weighting the projections prior to the filtered backprojection. Algorithms, such as generalized linear helical (GLH), Row-wise-full, Row-wise, high speed partial scan (HSPS), and others can be implemented in either form. A filtered backprojection algorithm is then used for the final image reconstruction.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
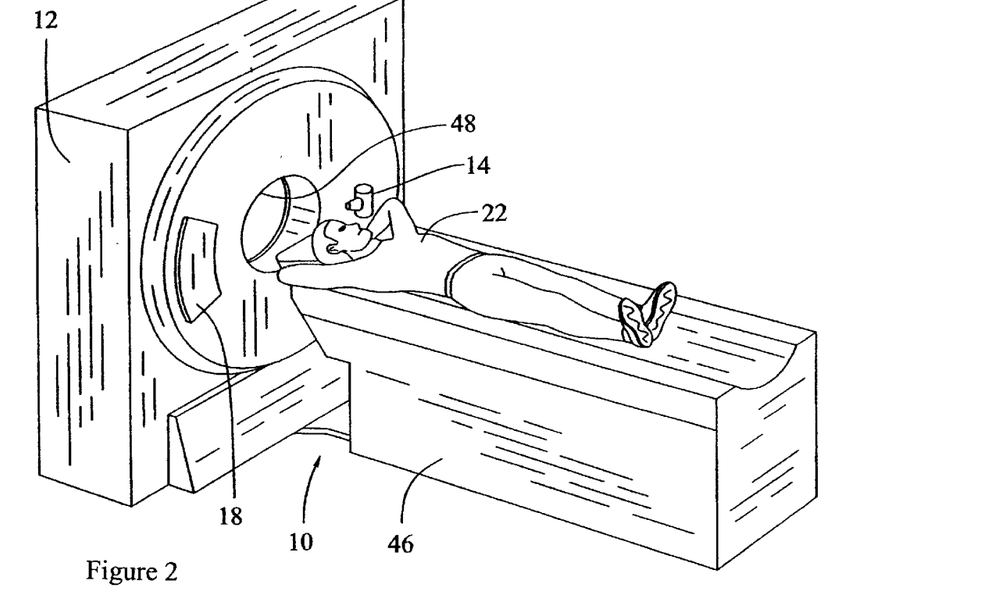
FIG. 2 is a pictorial view of a CT imaging system.
Figure 3:
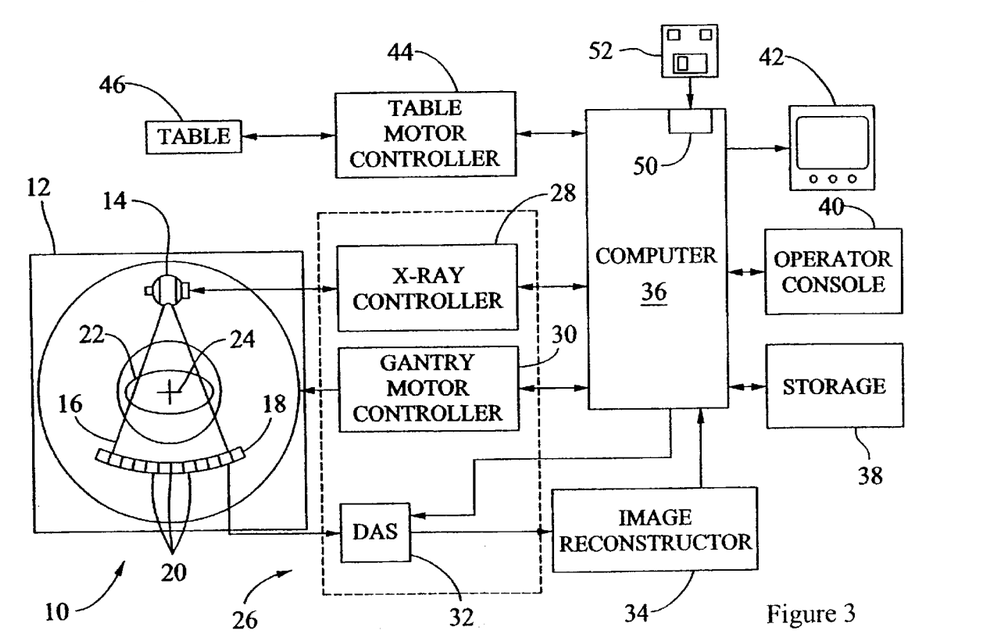
FIG. 3 is a block schematic diagram of the system illustrated in FIG. 2.

Referring to FIGS. 2 and 3, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 4:
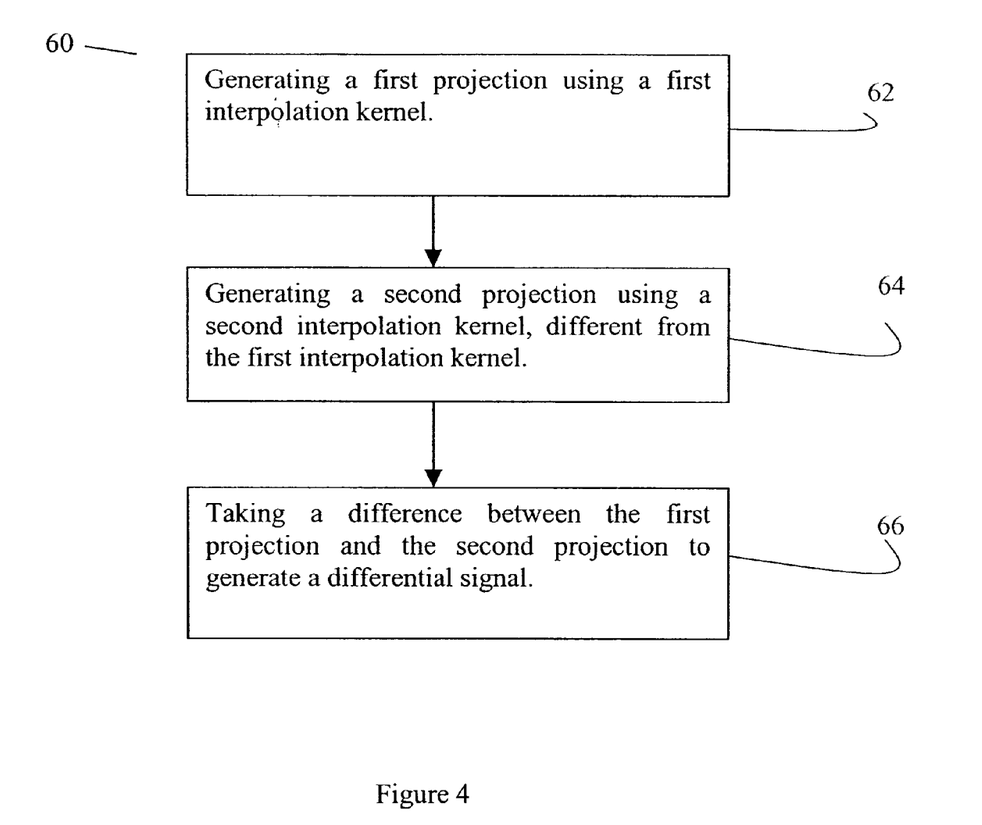
FIG. 4 is a flow diagram of a method for weighting projection data.

FIG. 4 is a flow diagram of a method 60 generating an image of an object 12 with scanning imaging system 10, wherein imaging system 10 is operating in at least one of a high speed data acquisition mode and a high quality data acquisition mode. Method 60 includes generating 62 a first projection using a first interpolation kernel, generating 64 a second projection using a second interpolation kernel, different from the first interpolation kernel, and taking 66 a difference between the first projection and the second projection to generate a differential signal.

In the exemplary embodiment, the interpolations described herein include at least one of a physical interpolation and a projection weighting. Generating 62 a first projection using a first interpolation kernel includes generating a first projection using a two-nearest-neighbor linear interpolation. In use, the first interpolation produces a good slice-sensitivity profile. In one embodiment, using high-speed data acquisition mode, (i.e. a high helical pitch), the first interpolation is carried out between two adjacent detector rows (not shown). In another embodiment, using high-quality data acquisition mode, the first interpolation is carried out between conjugate samples.

Generating 64 a second projection using a second interpolation kernel, different from the first interpolation kernel includes using at least one of a line interpolation weights with a z-smooth filter, a Hanning interpolation, and a high-order polynomial interpolation. The second interpolation kernel facilitates suppressing image interpolation artifacts, at the cost of slice-sensitivity profile broadening.

Figure 5:
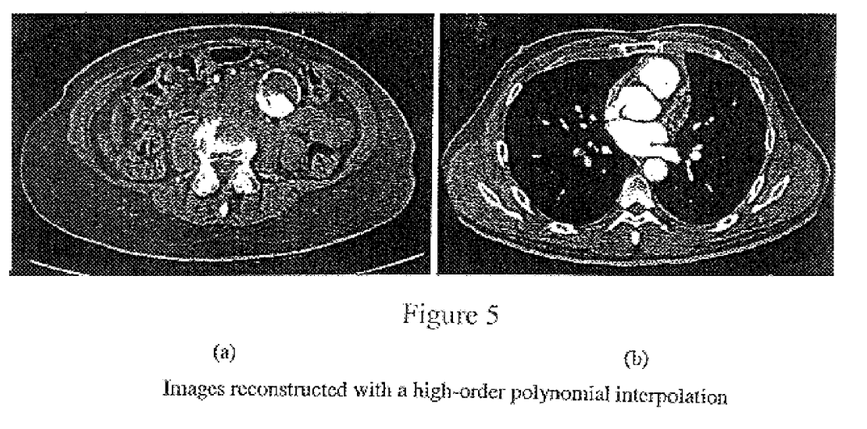
FIG. 5 is a sinogram view of an image reconstructed with a higher order polynomial.

FIG. 5 is a sinogram view of the same images illustrated in FIG. 1, reconstructed with a 3-point high-order polynomial. The images were reconstructed with the following coefficients, $w_n$:

$$q_n = c_0 + c_1\Delta^2 + c_2\Delta^4 \text{ and } w_n = \frac{q_n}{q_1 + q_2 + q_3} \quad (1)$$

where n=1, 2, or 3, $c_0$=2, $c_1$=−1.1877, $c_2$=0.1932, and wherein $\Delta$ is a normalized distance of a sample from a plane-of-reconstruction and equals an actual distance divided by a detector aperture. The images produced by the interpolation illustrated in Equation 1 have a degraded slice-sensitivity profile as described previously herein. However, compared to FIG. 1, the images shown in FIG. 5 illustrated that the algorithm offers reduced image artifacts.

In the exemplary embodiment, an adaptive interpolation approach is used instead of producing an image subsequent to the first interpolation. In use, a first projection using a first interpolation kernel is generated. A second projection using a second interpolation kernel, different from the first interpolation kernel, is then generated. A difference between the projection generated with the first interpolation kernel and the projection generated with the second interpolation kernel is taken to generate a differential signal in accordance with $$\delta p(\gamma, \beta) = |p_1(\gamma, \beta) - p_2(\gamma, \beta)| \quad (2)$$

where $p_1$ and $p_2$ are the interpolated projections with the first and second kernels, respectively.

A low-pass filtering is performed to the differential signal $\delta p$ to generate a filtered differential signal $\delta p'$ in accordance with $$\delta p'(\gamma, \beta) = \delta p(\gamma, \beta) * k(\gamma) \quad (3)$$

where k is a low-pass filter kernel and * represents the convolution operator. In one embodiment, the low-pass filter kernel is a box-car filter of 11 elements and facilitates suppressing fluctuations due to noise. In one embodiment, the low-pass filter is one-dimensional. In another embodiment, the low-pass filter can include, but is not limited to, a two-dimensional filter, and a three-dimensional filter, wherein the two-dimensional filter and the three-dimensional filter include a row direction and a projection angle, $\beta$.

The filtered differential signal $\delta p'$, is mapped to a scaling function s, for interpolation. In one embodiment, the mapping function is defined in accordance with $$s(\gamma, \beta) = \begin{cases} 0, & \delta p'(\gamma, \beta) \le t_{low} \\ \frac{\delta p'(\gamma, \beta) - t_{low}}{t_{high} - t_{low}}, & t_{low} < \delta p'(\gamma, \beta) \le t_{high} \\ 1, & \delta p'(\gamma, \beta) > t_{high} \end{cases} \quad (4)$$

where $t_{low}$ and $t_{high}$ are selected thresholds.

In one embodiment, using an 8×1.25 mm with a pitch of 13.4, wherein $t_{low}=500$, and $t_{high}=1000$, the adaptively interpolated projection, $P_i$, is defined according to $$p_i(\gamma, \beta) = [1 - s(\gamma, \beta)]p_1(\gamma, \beta) + s(\gamma, \beta)p_2(\gamma, \beta) \quad (5)$$

In one embodiment, additional weights, such as, but not limited to half-scan weights, may then be applied to the adaptively interpolated projection prior to a filtered backprojection process.

In another embodiment, different ways of producing the new projection based on the differential projection can be used. For example, the combination of $p_1$ and $p_2$ can be made using a nonlinear function.

In yet another embodiment, more than two projections are interpolated and more than one differential projections are calculated. Based on the differential projections, a final projection is produced for image reconstruction. Using the same notation as described previously herein, k interpolated projections $p_1, p_2, \ldots, p_k$ can be generated. Each projection is generated by interpolating the original projections with different kernels. For example, $p_1$ is produced with a linear interpolation kernel and $p_2$ to $p_k$ are generated with interpolation kernels described by equation (1) of different parameters. Once the new projections are produced, differential signals, $\delta p_j$, are produced based on the following equation:

$$\delta p_j = |p_1(\gamma, \beta) - p_j(\gamma, \beta)| \quad (6)$$

The final interpolated projection is a weighted sum of the projections wherein the weighting factors are determined by the differential signals:

$$p(\gamma, \beta) = \sum_{j=1}^{k} w_j(\gamma, \beta) p_j(\gamma, \beta) \quad (7)$$

Figure 6:
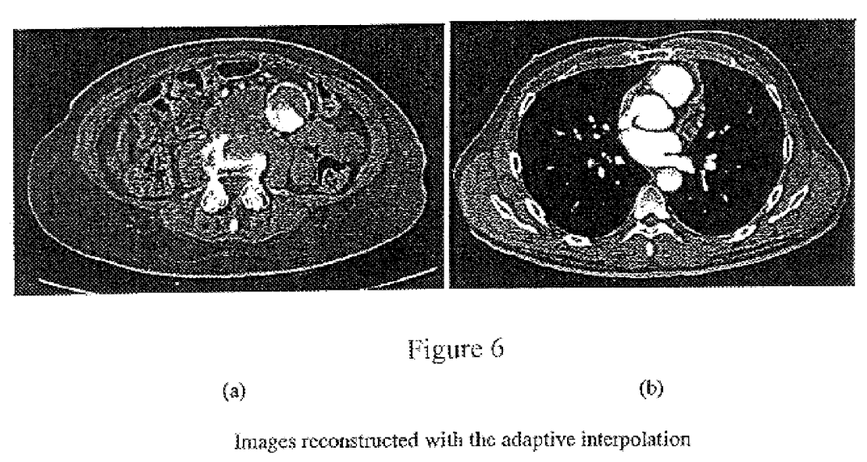
FIG. 6 is a sinogram view of an image reconstructed with an adaptive interpolation.

FIG. 6 shows the same scans shown in FIG. 5 reconstructed with the adaptive approach described herein. In use, the image artifacts suppression capability is approximately equal to that shown in FIG. 5 without a degradation in slice thickness.

Measurement of the slice-sensitivity profile has shown that the slice thickness of the adaptive approach described herein is approximately identical to the slice thickness obtained with the first interpolation. This is a 20% improvement over the second interpolation, thereby preserving the best properties of both interpolation approaches. The slice thickness is tabulated in Table 1, where filtering is full width at half maximum.

TABLE 1

|  | HSPS algorithm | High-order interpolation | Adaptive Interpolation |
| --- | --- | --- | --- |
| FWHM (mm) | 1.60 | 1.90 | 1.60 |

While the invention has been described in terms of various specific embodiments, those skilled in the art will recognize that the invention can be practiced with modification within the spirit and scope of the claims.

What is claimed is:

1. A method for generating an adaptively interpolated projection of an object with an imaging system, said method comprising:

generating a first projection using a first interpolation kernel;

generating a second projection using a second interpolation kernel, different from the first interpolation kernel; and taking a difference between the first projection and the second projection to generate a differential signal.

2. A method in accordance with claim 1 further comprising filtering the differential signal using a low-pass filter.

3. A method in accordance with claim 1 further comprising mapping the filtered differential signal to a scaling function to generate an adaptively interpolated projection.

4. A method in accordance with claim 1 further comprising applying additional weights to the adaptively interpolated projection.

5. A method in accordance with claim 1 further comprising filtering and backprojecting the adaptively interpolated projection.

6. A method in accordance with claim 1 wherein generating a first projection using a first interpolation kernel comprises generating a first projection using a two-nearest neighbor linear interpolation.

7. A method in accordance with claim 1 wherein generating a second projection using a second interpolation kernel, different from the first interpolation kernel comprises generating a second projection using at least one a Hanning interpolation, a line interpolation, and a high-order polynomial interpolation.

8. A method in accordance with claim 1 wherein said imaging system is operating in at least one of a high speed data acquisition mode and a high quality data acquisition mode.

9. A method in accordance with claim 3 wherein mapping the filtered differential signal to a scaling function to generate an adaptively interpolated projection comprises mapping the filtered differential signal to a scaling function in accordance with:

$$s(\gamma, \beta) = \begin{cases} 0, & \delta p'(\gamma, \beta) \leq t_{low} \\ \dfrac{\delta p'(\gamma, \beta) - t_{low}}{t_{high} - t_{low}}, & t_{low} < \delta p'(\gamma, \beta) \leq t_{high} \\ 1, & \delta p'(\gamma, \beta) > t_{high}, \end{cases}$$

where:

$\delta p'(\gamma,\beta)$ is the filtered differential signal;

$t_{low}$ is a selected threshold; and $t_{high}$ is a selected threshold.

10. A method in accordance with claim 3 wherein mapping the filtered differential signal to a scaling function to generate an adaptively interpolated projection comprises generating an adaptively interpolated projection by taking a linear combination of the first projection and the second projection.

11. A method in accordance with claim 10 wherein generating an adaptively interpolated projection comprises generating an adaptively interpolated projection in accordance with:

$$p_i(\gamma,\beta)=[1-s(\gamma,\beta)]p_i(\gamma,\beta)+s(\gamma,\beta)p_2(\gamma,\beta)$$

where:

$\delta p(\gamma,\beta)$ is the scaling function;

$p_1(\gamma,\beta)$ is the first projection generated with the first interpolation kernel; and $p_2(\gamma,\beta)$ is the second projection generated with the second interpolation kernel.

12. A method in accordance with claim 3 wherein mapping the filtered differential signal to a scaling function to generate an adaptively interpolated projection comprises generating an adaptively interpolated projection by taking a non-linear combination of the first projection and the second projection.

13. A method in accordance with claim 1 further comprising:

generating a third projection using a third interpolation kernel; and taking a difference between the first projection and the second projection, and taking the difference between the first projection and the third projection to generate multiple differential signals.

14. A method for generating an adaptively interpolated projection of an object with a scanning imaging system wherein the imaging system is operating in at least one of a high speed data acquisition mode and a high quality data acquisition mode, said method comprising:

generating a first projection using a first interpolation kernel;

generating a second projection using a second interpolation kernel, different from the first interpolation kernel, wherein the second interpolation kernel includes at least one of a Hanning interpolation, a line interpolation, and a high-order polynomial interpolation;

taking a difference between the first projection and the second projection to generate a differential signal;

filtering the differential signal using a low-pass filter using at least one of a one-dimensional filter, a two-dimensional filter, and a three-dimensional filter;

mapping the filtered differential signal to a scaling function to generate an adaptively interpolated projection in accordance with:

$$s(\gamma, \beta) = \begin{cases} 0, & \delta p'(\gamma, \beta) \leq t_{low} \\ \dfrac{\delta p'(\gamma, \beta) - t_{low}}{t_{high} - t_{low}}, & t_{low} < \delta p'(\gamma, \beta) \leq t_{high} \\ 1, & \delta p'(\gamma, \beta) > t_{high}, \end{cases}$$

where:

$\delta p'(\gamma,\beta)$ is the filtered differential signal;

$t_{low}$ is a selected threshold; and $t_{high}$ is a selected threshold;

generating an adaptively interpolated projection comprises generating an adaptively interpolated projection in accordance with:

$$p_i(\gamma,\beta)=[1-s(\gamma,\beta)]p_i(\gamma,\beta)+s(\gamma,\beta)p_2(\gamma,\beta)$$

where:

$\delta p(\gamma,\delta)$ is the scaling function;

$p_1(\gamma,\beta)$ is the first projection generated with the first interpolation kernel; and $p_2(\gamma,\beta)$ is the second projection generated with the second interpolation kernel applying additional weights to the adaptively interpolated projection; and filtering and backprojecting the adaptively interpolated projection.

15. A computer to generate an adaptively interpolated projection of an object with a scanning imaging operable in at least one of a high speed data acquisition mode and a high quality data acquisition mode, said computer programmed to:

generate a first projection using a first interpolation kernel;

generate a second projection using a second interpolation kernel, different from the first interpolation kernel; and take a difference between the first projection and the second projection to generate a differential signal.

16. A computer in accordance with claim 15 wherein said computer further programmed to filter the differential signal using a low-pass filter.

17. A computer in accordance with claim 16 wherein said computer further programmed to map the filtered differential signal to a scaling function to generate an adaptively interpolated projection.

18. A computer in accordance with claim 15 wherein said computer further programmed to:

apply additional weights to the adaptively interpolated projection; and filter and backproject the adaptively interpolated projection.

19. A computer in accordance with claim 15 wherein to generate a first projection using a first interpolation kernel, said computer further programmed to generate a first projection using a two-nearest neighbor linear interpolation.

20. A computer in accordance with claim 15 wherein to generate a second projection using a second interpolation kernel, different from the first interpolation kernel, said computer further programmed to generate a second projection using at least one of a Hanning interpolation, a line interpolation, and a high-order polynomial interpolation.

21. A computer in accordance with claim 17 wherein to map the filtered differential signal to a scaling function to generate an adaptively interpolated projection, said computer further programmed to map the filtered differential signal to a scaling function in accordance with $$s(\gamma, \beta) = \begin{cases} 0, & \delta p'(\gamma, \beta) \leq t_{low} \\ \frac{\delta p'(\gamma, \beta) - t_{low}}{t_{high} - t_{low}}, & t_{low} < \delta p'(\gamma, \beta) \leq t_{high} \\ 1, & \delta p'(\gamma, \beta) > t_{high}, \end{cases}$$

where:
$\delta p'(\gamma,\beta)$ is the filtered differential signal;
$t_{low}$ is a selected threshold; and
$t_{high}$ is a selected threshold.

22. A computer in accordance with claim 17 wherein to map the filtered differential signal to a scaling function to generate an adaptively interpolated projection, said computer further programmed to generate an adaptively interpolated projection in accordance with:

$$p_i(\gamma,\beta) = [1 - s(\gamma,\beta)]p_1(\gamma,\beta) + s(\gamma,\beta)p_2(\gamma,\beta)$$

where:
$\delta p(\gamma,\delta)$ is the scaling function;
$p_1(\gamma,\beta)$ is the first projection generated with the first interpolation kernel; and
$p_2(\gamma,\beta)$ is the second projection generated with the second interpolation kernel.

23. A computer to generate an adaptively interpolated projection of an object with a scanning imaging system wherein the imaging system is operating in at least one of a high speed data acquisition mode and a high quality data acquisition mode, said computer programmed to:
generate a first projection using a first interpolation kernel;
generate a second projection using a second interpolation kernel, different from the first interpolation kernel, wherein the second interpolation kernel includes at least one of a Hanning interpolation, a line interpolation, and a high-order polynomial interpolation;
take a difference between the first projection and the second projection to generate a differential signal:

$$\delta p(\gamma,\beta) = |p_1(\gamma,\beta) - p_2(\gamma,\beta)|,$$

where:
$p_1(\gamma,\beta)$ is the first projection generated with the first interpolation kernel; and
$p_2(\gamma,\beta)$ is the second projection generated with the second interpolation kernel;
filter the differential signal;
map the filtered differential signal to a scaling function to generate an adaptively interpolated projection in accordance with:

$$s(\gamma, \beta) = \begin{cases} 0, & \delta p'(\gamma, \beta) \leq t_{low} \\ \frac{\delta p'(\gamma, \beta) - t_{low}}{t_{high} - t_{low}}, & t_{low} < \delta p'(\gamma, \beta) \leq t_{high} \\ 1, & \delta p'(\gamma, \beta) > t_{high}, \end{cases}$$

where:
$\delta p'(\delta,\beta)$ is the filtered differential signal;
$t_{low}$ is a selected threshold; and
$t_{high}$ is a selected threshold;
generate an adaptively interpolated projection comprises generating an adaptively interpolated projection in accordance with:

$$p_i(\gamma,\beta) = [1 - s(\gamma,\beta)]p_1(\gamma,\beta) + s(\gamma,\beta)p_2(\gamma,\beta)$$

where:
$\delta p(\gamma,\beta)$ is the scaling function;
$p_1(\gamma,\beta)$ is the first projection generated with the first interpolation kernel; and
$p_2(\gamma,\beta)$ is the second projection generated with the second interpolation kernel
apply additional weights to the adaptively interpolated projection; and
filter and backproject the adaptively interpolated projection.

24. A computed tomographic (CT) imaging system for generating an adaptively interpolated projection of an object, said CT system comprising:
a detector array;
at least one radiation source; and
a computer coupled to said detector array and said radiation source, said computer configured to:
generate a first projection using a first interpolation kernel;
generate a second projection using a second interpolation kernel, different from the first interpolation kernel;
take a difference between the first projection and the second projection to generate a differential signal;
filter the differential signal using a low-pass filter; and
map the filtered differential signal to a scaling function to generate an adaptively interpolated projection.

25. A CT system in accordance with claim 24, wherein said computer further configured to apply additional weights to the adaptively interpolated projection.

26. A CT system in accordance with claim 24, wherein said computer further configured to filter and backproject the adaptively interpolated projection.

27. A CT system in accordance with claim 24 wherein to generate a first projection using a first interpolation kernel, said computer further configured to generate a first projection using a two-nearest neighbor linear interpolation.

28. A CT system in accordance with claim 24 wherein to generate a second projection using a second interpolation kernel, different from the first interpolation kernel, said computer further configured to generate a second projection using at least at least one of a Hanning interpolation, a line interpolation, and a high-order polynomial interpolation.

29. A CT system in accordance with claim 24 wherein said CT system is operating in at least one of a high speed data acquisition mode and a high quality data acquisition mode.

30. A CT system in accordance with claim 24 wherein to map the filtered differential signal to a scaling function to generate an adaptively interpolated projection, said computer further configured to map the filtered differential signal to a scaling function in accordance with:

$$s(\gamma, \beta) = \begin{cases} 0, & \delta p'(\gamma, \beta) \leq t_{low} \\ \frac{\delta p'(\gamma, \beta) - t_{low}}{t_{high} - t_{low}}, & t_{low} < \delta p'(\gamma, \beta) \leq t_{high} \\ 1, & \delta p'(\gamma, \beta) > t_{high}, \end{cases}$$

where:

$\delta p'(\gamma,\beta)$ is the filtered differential signal;

$t_{low}$ is a selected threshold; and $t_{high}$ is a selected threshold.

31. A CT system in accordance with claim 24 wherein to map the filtered differential signal to a scaling function to generate an adaptively interpolated projection, said computer further configured to generate an adaptively interpolated projection in accordance with $$p_i(\gamma,\beta)=[1-s(\gamma,\beta)]p_1(\gamma,\beta)+s(\gamma,\beta)p_2(\gamma,\beta)$$

where:

$\delta p(\gamma,\beta)$ is the scaling function;

$p_1(\gamma,\beta)$ is the first projection generated with the first interpolation kernel; and $p_2(\gamma,\beta)$ is the second projection generated with the second interpolation kernel.

32. A computed tomographic (CT) imaging system for generating an adaptively interpolated projection of an object wherein said CT system is operating in at least one of a high speed data acquisition mode and a high quality data acquisition mode, said CT system comprising:

a detector array;

at least one radiation source; and a computer coupled to said detector array and said radiation source, said computer configured to:

generate a first projection using a first interpolation kernel;

generate a second projection using a second interpolation kernel, different from the first interpolation kernel using at least one of a Hanning interpolation, a line interpolation, and a high-order polynomial interpolation;

take a difference between the first projection and the second projection to generate a differential signal;

filter the differential signal using at least one of a one-dimensional filter, a two-dimensional filter, and a three-dimensional filter;

map the filtered differential signal to a scaling function to generate an adaptively interpolated projection in accordance with:

$$s(\gamma,\beta) = \begin{cases} 0, & \delta p'(\gamma,\beta) \le t_{low} \\ \dfrac{\delta p'(\gamma,\beta) - t_{low}}{t_{high} - t_{low}}, & t_{low} < \delta p'(\gamma,\beta) \le t_{high} \\ 1, & \delta p'(\gamma,\beta) > t_{high}, \end{cases}$$

where:

$\delta p'(\gamma,\beta)$ is the filtered differential signal;

$t_{low}$ is a selected threshold; and $t_{high}$ is a selected threshold;

generate an adaptively interpolated projection comprises generating an adaptively interpolated projection in accordance with:

$$p_i(\gamma,\beta)=[1-s(\gamma,\beta)]p_i(\gamma,\beta)+s(\gamma,\beta)p_2(\gamma,\beta)$$

where:

$\delta p(\gamma,\beta)$ is the scaling function;

$p_1(\gamma,\beta)$ is the first projection generated with the first interpolation kernel; and $p_2(\gamma,\beta)$ is the second projection generated with the second interpolation kernel;

apply additional weights to the adaptively interpolated projection; and filter and backproject the adaptively interpolated projection.

\* \* \* \* \*

UNITED STATES PATENT AND TRADEMARK OFFICE
CERTIFICATE OF CORRECTION

PATENT NO. : 6,587,537 B1  Page 1 of 1
DATED : July 1, 2003
INVENTOR(S) : Jiang Hsieh It is certified that error appears in the above-identified patent and that said Letters Patent is hereby corrected as shown below:

Column 6,
Line 59, delete "one a" insert therefor -- one of a --.

Column 7,
On the right side of the formula, delete "$^t$low" insert therefor -- $t_{low}$ --.

Column 8,
On the right side of the formula, delete "$^t$low" insert therefor -- $t_{low}$ --.
Line 22, delete "$(\gamma,\delta)$" insert therefor -- $(\gamma,\beta)$ --.

Column 9,
On the right side of the formula, delete "$^t$low" insert therefor -- $t_{low}$ --.
Line 25, delete "$(\gamma,\delta)$" insert therefor -- $(\gamma,\beta)$ --.
Line 61, right side of the formula, delete "$^t$low" insert therefor -- $t_{low}$ --.
Line 66, delete "$(\delta,\beta)$" insert therefor -- $(\gamma,\beta)$ --.

Column 10,
Line 50, delete "at least at least" insert therefor -- at least --.
On the right of the formula, delete "$^t$low" insert therefor -- $t_{low}$ --.

Column 12,
On the right side of the formula, delete "$^t$low" insert therefor -- $t_{low}$ --.

Signed and Sealed this

Thirtieth Day of September, 2003

JAMES E. ROGAN
*Director of the United States Patent and Trademark Office*